United States Patent [19]

Brenner

[11] 4,046,813
[45] Sept. 6, 1977

[54] PROCESS FOR PRODUCING KETOISOPHORONE

[75] Inventor: Wolf Brenner, Fullinsdorf, Switzerland

[73] Assignee: Hoffmann-La Roche Inc., Nutley, N.J.

[21] Appl. No.: 563,040

[22] Filed: Mar. 28, 1975

[30] Foreign Application Priority Data

Apr. 11, 1974 Switzerland ............... 5187/74

[51] Int. Cl.$^2$ ................................. C07C 45/00
[52] U.S. Cl. ..................................... 260/586 P
[58] Field of Search .......................... 260/586 P

[56] References Cited

U.S. PATENT DOCUMENTS

| 2,819,298 | 1/1958 | Isler et al. | 260/586 P |
| 2,827,481 | 3/1958 | Isler et al. | 260/586 P |
| 3,380,456 | 8/1965 | Roberts et al. | 260/586 P |
| 3,773,836 | 11/1973 | Hall | 260/586 P |
| 3,931,327 | 1/1976 | Stuckler et al. | 260/586 P |
| 3,944,620 | 3/1976 | Becker et al. | 260/586 P |
| 3,960,966 | 6/1976 | Widmer et al. | 260/586 P |
| 4,010,205 | 3/1977 | Becker et al. | 260/586 P |

FOREIGN PATENT DOCUMENTS 1,066,709  4/1967  United Kingdom ............ 260/586 P

OTHER PUBLICATIONS

Hawkins, "J. Chem. Soc.," 1955, pp. 3288-3290 (1955).

Primary Examiner—Norman Morganstern
Attorney, Agent, or Firm—Samuel L. Welt; Bernard S. Leon; William H. Epstein

[57] ABSTRACT

Process for producing ketoisophorone from β-isophorone by oxidation utilizing a metal salt catalyst and an organic nitrogen base.

8 Claims, No Drawings

PROCESS FOR PRODUCING KETOISOPHORONE

BACKGROUND OF THE INVENTION

Attempts have already been made to oxidize α,β-or β,γ-unsaturated aldehydes or ketones with the aid of a copper compound in the presence of a heterocyclic nitrogen base, which forms a complex compound with the catalyst, and an alkylamine.

β-Isophorone [3,5,5-trimethyl-cyclohex-3-en-1-one] has been oxidized to ketoisophorone [3,5,5-trimethyl-cyclohex-2-en-1,4-dione] for example with the aid of copper (ii) nitrate in the presence of pyridine and triethylamine in a nitrogen atmosphere. However, in this oxidation, by-products are formed to a considerable degree. These by-products including hydroxyisophorone [3,5,5-trimethyl-4-hydroxy-cyclohex-2-en-1-one], the difficulty separable α-isophorone [3,5,5-trimethyl-cyclohex-2-en-1-one] and dehydrodimers of isophorone. The yield of ketoisophorone which can be isolated by these procedures is very low, namely 30%. Therefore, a procedure is desired whereby the oxidation of β-isophorone to ketoisophorone can be carried out systematically without the formation of undesired by-products and in high yields.

SUMMARY OF THE INVENTION

In accordance with this invention, it has been found that β-isophorone can be oxidized to ketoisophorone systematically in high yields, without the formation of undesirable and hard to separate by-products by oxidizing β-isophorone which has the formula:

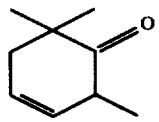

with oxygen or an oxygen containing gas in the presence of a nitrogen containing organic base and as a catalyst, a salt of a metal selected from the group consisting of led, vanadium, chromium, manganese, iron or cobalt.

The product produced by this oxidation is ketoisophorone which has the formula:

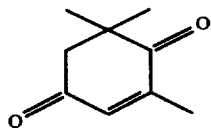

DETAILED DESCRIPTION

The present invention is based on the foregoing finding and is accordingly concerned with a process for the manufacture of ketoisophorone by the oxidation of β-isophorone with oxygen or an oxygen-containing gas with the aid of a catalyst, said process comprising carrying out the oxidation in the presence of an organic nitrogen base with a lead, vanadium, chromium, manganese, iron or cobalt salt as a catalyst.

In carrying out this invention, any salt of lead, vanadium, chromium, manganese, iron or cobalt can be utilized as the catalyst. A preferred embodiment of the process provided by the present invention consists in carrying out the oxidation with a vanadium, manganese or iron salt.

The salts of lead, vanadium, chromium, manganese, iron and cobalt used as the oxidation catalysts can be classified as follows:
salts of acids,
salts of enols (salts of 1,3-diketones),
salts of alcohols (alcoholates).

Any conventional organic or inorganic acid which forms a salt with the above metals can be utilized as the catalyst in this invention. Among the preferred acid salts are salts of weak acids, especially weak organic acids such as aroic acids, alkanoic acids and aryl alkanoic acids. Examples of such salts are:
lead naphthenate, lead acetate;
vanadium naphthenate, vanadium acetate;
chromium naphthenate, chromium acetate;
manganese naphthenate, manganese acetate;
iron naphthenate, iron acetate, iron propionate;
cobalt acetate, cobalt propionate.

Of the previously mentioned metal salts of weak organic acids, vanadium naphthenate, manganese acetate and iron naphthenate are especially preferred as catalysts.

Among the metal salts are metal salts or inorganic acids, especially strong inorganic acids. Among the preferred acis are hydrohalic acids, sulfuric acids, phosphoric acids, etc. Among the inorganic acid salts of these metals are vanadium oxysulfate and the chlorides and sulfates of iron [iron (III) chloride and iron (II) sulfate are especially preferred]. Any salt of the above metals with an enol can be utilized to carry out this oxidation step of this invention. Among the preferred enols are the enols formed from diketones of aliphatic saturated hydrocarbons such as those diketones of the formula:

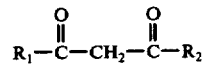

wherein $R_1$ and $R_2$ are lower alkyl.
Examples of salts of enols [1,3-diketones] are:
vanadium acetylacetonate;
chromium acetylacetonate;
manganese acetylacetonate;
iron acetylacetonate;
cobalt acetylacetonate.

Any salt of the above metals with an alcohol (alcoholate) can be utilized to carry out the oxidation step of this invention. Anomg the preferred alcohols are those alcohols of the aliphatic saturated hydrocarbons such as the lower alkanols.

Examples of salts of alcohols (alcoholates) are:
vanadium isopropylate, vandium n-butylate,
manganese butylate;
iron propylate;
cobalt hexanolate.

Of the three named groups of metal salts,
vanadium acetylacetonate, vanadium isopropylate, vanadium oxysulphate,
managanse acetylacetonate, manganese acetate and iron (III) acetylacetonate
are preferred catalysts.

The oxidation in accordance with the invention is carried out in the presence of an organic nitrogen base. Any conventional organic nitrogen base can be utilized in carrying out this invention. The presence of one or more bases increases the yield of the desired oxidation product and extensively supresses the formation of undesirable by-products.

Among the organic nitrogen bases are the organic amine bases such as the primary, secondary or tertiary amine bases. Among the preferred bases which can be used in the present process are included:

cyclic nitrogen bases, especially aromatic nitrogen bases such as pyridine and its homologues (e.g. 2-methyl-4-ethyl-pyridine) and also N-heterocyclic bases (e.g. piperidine and morpholine);

aliphatic nitrogen bases which include mono, di or tertiary alkyl or alkanol amines e.g. triethylamine and ethanolamine.

Mixtures of cyclic and aliphatic nitrogen bases can also be used in the oxidation.

The oxidation can be carried out in either the presence or absence of a solvent. If the catalyst used is at least partly soluble in the substrate (e.g. vanadium isopropylate in β-isophorone), then the addition of a solvent is superfluous. Furthermore, the base utilized can serve as the solent. In general, it is recommended, however, to add a solvent to the oxidation components. If desired, any conventional inert organic solvent can be utilized in carrying out this oxidation of this invention. Among the preferred solvents are included:

alcohols (e.g. methanol, ethanol, isopropanol, butanol, ethyleneglycol and diethyleneglycol);
ketones (e.g. acetone and butanone);
aromatic hydrocarbons (e.g. benzene and toluene);
dimethylformamide, dimethyl sulfoxide and ethylenglycol monomethyl ether;
pyridine and its homologues;
and the ketoisophorone resulting in the oxidation.

Of the foregoing solvents, dimethylformamide, ethyleneglycolmonomethyl ether, ketoisophorone and pyridine and its homologues are preferred.

The gas which is utilized to oxidize the β-isophorone in accordance with this invention can be oxygen or any oxygen containing gas, for example air. However, if desired, the oxygen content of the air can be reduced by adding nitrogen to the air. On the other hand, air enriched with oxygen can be utilized as the oxidation medium. On the other hand, pure oxygen can be utilized as the gaseous medium to affect oxidation in accordance with this invention.

In carrying out this reaction, temperature and pressure are not critical and this reaction can be carried out at room temperature and atmospheric pressure. Generally, it is preferred to maintain the temperature during the oxidation at from about −20° to about +120° C., particularly from about +20° to about +100° C.

In accordance with a preferred embodiment, the temperature can be expediently controlled according to the strength of the base so that the rapidly occurring and strongly exothermic oxidation can be kept under control. When the oxidation is carried out in the presence of piperidine or triethylamine, for example, it is generally preferred to cool the mixture to about +20° C. to about −20° C. When the oxidation is carried out in the presence of pyridine, the temperature can be increased up to about 120° C. Temperatures greater than 120° C. generally promote the formation of undesired oligomers and oxidative decomposition products of ketoisophorone. Therefore, it is generally preferred to utilize temperatures of 120° C. or below.

The oxidation is preferably carried out with oxygen or an oxygencontaining gas [air]. The partial pressure is not critical. It can lie in a range of from 1 to about 10 atmospheres, preferably at 1–3 atmospheres. An increase in the oxygen concentration generally causes a reduction in the formation of dimeric products.

The term "halogen", as utilized in the instant specification, denotes all four halogens, i.e., chlorine, bromine, iodine and fluorine, with chlorine and bromine being preferred. The term "alkyl" denotes both straight chain and branched chain alkyl groups containing from 1 to 18 carbon atoms. Among the preferred alkyl groups are the lower alkyl groups containing from 1 to 7 carbon atoms such as methyl, ethyl, isopropyl and 2-methylpropyl. The term "alkaonols" as used throughout this specification denotes alkyl mono alcohols preferably lower alkyl mono alkanols (lower alkanols) containing from 1 to 7 carbon atoms such as methanol, propanol, isopropanol, ethanol, etc. The term "alkanoic acid" denotes saturated aliphatic monocarboxylic acids containing from 2 to 18 carbon atoms. The preferred alkanoic acids are the lower alkanoic acids which contain from 2 to 7 carbon atoms such as acetic acid, propionic acid or butric acid.

The term "N-heterocyclic bases" designates N-heterocyclic bases containing preferably 5 to 6 membered rings which contain a nitrogen atom in the ring and which can, if desired, contain a further hetero atom selected from the group consisting of oxygen or nitrogen. Among the preferred N-heterocyclic bases are included pyrrolidine, piperidine or morpholine.

The term "alkanoyloxy" designates derivatives of alkanecarboxylic acids containing from 2 to 20 carbon atoms. Among the preferred lower alkanoyloxy groups are included lower alkanoyloxy groups containing from 2 to 7 carbon atoms such as acetyloxy, propionyloxy and pivalyloxy.

The term "aryl" as used throughout the application included mononuclear aryl groups such as phenyl which can be unsubstituted or substituted in one or more positions with a lower alkyl, or polynuclear aryl groups such as naphthyl, anthryl, phenanthryl, azulyl, etc. which may be unsubstituted or substituted with one or more of the aforementioned groups. The term "aroyloxy or aroic acids" comprehends groups wherein the aryl moiety is defined as above. Among the preferred aroic acids is benzoic acid.

The term "aroic acid" designates an acid of the formula:

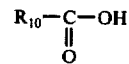

where $R_{10}$ is aroyl as defined above. The term "aryl lower alkanoic acid" designates an acid where aryl and lower alkanoic acid are defined as above.

The homologues of pyridine are defined as pyridine which is substituted in one or more positions with a lower alkyl group.

The following Examples are illustrative but not limitative of the present invention:

EXAMPLE 1

3,8 g. of lead acetate in 100 ml. of pyridine are treated with 69 g. of β-isophorone. The mixture is gassed with oxygen at 70° C. for 2 hours with intensive stirring and subsequently worked up by distillation. [b.p. 62°–64° C, 0,2 Torr]. The conversion of β-isophorone used amounts to 31 g. corresponding 45%. Ketoisophorone is obtained in a yield of 26 g. corresponding to 76%.

EXAMPLE 2

1,7 g. of vanadium isopropylate in 100 ml. of methanol and 50 ml. of pyridine are treated with 69 g. of β-isophorone. The mixture is gassed with oxygen at 40° C. for 2 hours with intensive stirring and subsequently worked up by distillation. The yield of crystalline ketoisophorone amounts to 53,2 g. corresponding to 70% [Conversion: 100%]

EXAMPLE 3

55 g. of vanadium acetylacetonate in 800 ml. of pyridine are treated with 552 g. of β-isophorone. The mixture is gassed with oxygen at 70° C. for 3,5 hours with intensive stirring and subsequently worked up by distillation. The yield of crystalline ketoisophorone amounts to 553 g. corresponding to 91%. [Conversion: 100%].

EXAMPLE 4

3,5 g. of chromium (III) acetylacetonate in 100 ml. of pyridine are treated with 69 g. of β-isophorone. The mixture is gassed with oxygen at 70° C. for 2 hours with intensive stirring and subsequently worked up by distillation. The conversion of β-isophorone used amounts to 49,6 g. corresponding to 72%. Ketoisophorone is obtained in a yield of 41 g. corresponding to 75%.

EXAMPLE 5

2,5 g. of manganese acetate in 200 ml. of pyridine are treated with 69 g. of β-isophorone. The mixture is gassed with oxygen at 60° C. for 90 minutes and subsequently worked up by distillation. The yield of crystalline ketoisophorone amounts to 64,6 g. corresponding to 85%. [Conversion: 100%].

EXAMPLE 6

3,5 g. of iron (III) acetylacetonate in 35 ml. of pyridine and 25 ml. of dimethylformamide are treated with 69 g. of β-isophorone. The mixture is gassed with oxygen at 55° C. for 60 minutes and subsequently worked up by distillation. The yield of crystalline ketoisophorone amounts to 58,5 g. corresponding to 77%. [Conversion: 100%].

EXAMPLE 7

2,5 g. of cobalt acetate in 100 ml. of pyridine are treated with 69 g. of β-isophorone. The mixture is gassed with oxygen at 70° C. for 2 hours and subsequently worked up by distillation. The conversion of β-isophorone used amounts to 64 g. corresponding to 93%. Ketoisophorone is obtained in a yield of 48 g. corresponding to 68%.

What I claim is:

1. A process for oxidizing β-isophorone to ketoisophorone comprising oxidizing, in the presence of an organic aromatic nitrogen base, β-isophorone with oxygen or an oxygen containing gas utilizing as a catalyst a salt of a metal selected from the group consisting of lead, vanadium, chromium, manganese, iron or cobalt.

2. The process of claim 1, wherein said metal is vanadium, manganese or iron.

3. The process of claim 1, wherein said base is pyridine.

4. The process of claim 1, wherein the salt is an enol salt of vanadium, chromium, manganese, iron or cobalt.

5. The process or claim 4, wherein the enol salt is vanadium acetylacetonate, chromium acetylacetonate, manganese acetylacetonate, iron acetylacetonate or cobalt acetylacetonate.

6. The process of claim 1, wherein the oxidation is carried out in the presence of an inert organic solvent.

7. The process of claim 6, wherein the solvent is pyridine.

8. The process of claim 1, wherein the oxidation is carried out at a temperature of from about 20° to about 100° C.

* * * * *